United States Patent [19]

Vanlerberghe et al.

[11] Patent Number: 4,620,037
[45] Date of Patent: Oct. 28, 1986

[54] SEQUENCED SURFACTANT OLIGOMERS, PROCESS FOR PREPARING THE SAME AND COMPOSITIONS CONTAINING THE SAME

[75] Inventors: Guy Vanlerberghe, Claye-Souilly; Henri Sebag, Paris, both of France

[73] Assignee: L'Oreal, Paris, France

[21] Appl. No.: 539,743

[22] Filed: Oct. 6, 1983

Related U.S. Application Data

[62] Division of Ser. No. 87,794, Oct. 24, 1979, Pat. No. 4,491,534, which is a division of Ser. No. 815,847, Jul. 14, 1977, Pat. No. 4,199,562.

[30] Foreign Application Priority Data

Jul. 16, 1976 [LU] Luxembourg ............................ 75406

[51] Int. Cl.$^4$ .................... C07C 147/02; C07C 147/14
[52] U.S. Cl. .......................................... 568/36; 568/45; 568/46; 568/50; 252/351; 252/357
[58] Field of Search ................. 568/36, 45, 46, 50; 252/357, 351

[56] References Cited

U.S. PATENT DOCUMENTS

| | | | |
|---|---|---|---|
| 2,677,700 | 5/1954 | Jackson et al. | 568/36 |
| 3,454,646 | 7/1969 | Patton, Jr. et al. | 568/36 |
| 3,576,906 | 4/1971 | Hickner et al. | 260/849 |
| 3,821,306 | 6/1974 | Farber | 260/239 E |
| 4,105,580 | 8/1978 | Sebag et al. | 568/46 |
| 4,138,427 | 2/1979 | Vanlerberghe et al. | 568/36 |
| 4,906,048 | 9/1985 | Vanlerberghe et al. | 568/46 |

OTHER PUBLICATIONS

Chem. Abstracts–Fats, Waxes, and Detergents, 27, 1961, 19281+English translation of article of T. Kuwamura (Kobunshi Kagaku 17, pp. 175–182 (1960)).

Primary Examiner—George F. Lesmes
Assistant Examiner—S. A. Gibson
Attorney, Agent, or Firm—Cushman, Darby & Cushman

[57] ABSTRACT

Sequenced oligomer surfactant has the formula:

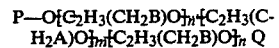

wherein one of P and Q represents hydrogen and the other represents alkyl having 1–20 carbon atoms; A represents R—CH$_2$— or R'—O— wherein R is alkyl having 4–16 carbon atoms and R' is alkyl having 4–20 carbon atoms; B is selected from OH, R$_1$R$_2$N, R$_1$R$_2$N→O, R$_1$R$_2$N—O$^\oplus$HV$^\ominus$, K$_1$R$_2$N$^\oplus$HV$^\ominus$, R$_1$R$_2$R$_3$N$^\oplus$Z$^\ominus$ and R$_4$S→(O)a, wherein R$_1$ and R$_2$ represent alkyl or hydroxyalkyl, R$_3$ is methyl or ethyl, R$_4$ is alkyl, hydroxyalkyl or dihydroxyalkyl, Z$^\ominus$ is an anion selected from HSO$_3^\ominus$, CH$_3$SO$_3^\ominus$, CH$_3$SO$_4^\ominus$ and CH$_3$—C$_6$H$_4$—SO$_3^\ominus$, R$_1$R$_2$N$^\oplus$HV$^\ominus$ and R$_1$R$_2$N—O$^\oplus$HV$^\ominus$ represent a salt of an amine or amine oxide, a is 0 or 1; m is a number from 2–10; and n and n' are numbers from 2–25, with one of n and n' capable of being O.

The oligomer surfactants are employed in cosmetic and pharmaceutical compositions.

10 Claims, No Drawings

SEQUENCED SURFACTANT OLIGOMERS, PROCESS FOR PREPARING THE SAME AND COMPOSITIONS CONTAINING THE SAME

This is a division of application Ser. No. 087,794, filed Oct. 24, 1979, now U.S. Pat. No. 4,491,534, which in turn is a division of application Ser. No. 815,847, filed July 14, 1977, now U.S. Pat. No. 4,199,562.

The present invention relates to new sequenced oligomer surfactants comprised of lipophilic sequences (L) and hydrophilic sequences (Hy), and which can be schematically represented by the formulas: L—Hy (1) or Hy—L—Hy (2).

There are presently known many surface active agents constituted by a fatty aliphatic hydrocarbon or aryl-aliphatic hydrocarbon lipophilic chain containing 8–18 carbon atoms, linked to a hydrophilic sequence.

These products have found numerous applications in the most diverse fields. They are varied in structure and it has been noted that their properties are limited by the nature of the lipophilic portion thereof.

In order to expand their properties, it has been proposed to replace the hydrocarbon chain of conventional surface active agents with a lipophilic sequence obtained by the polymerization of an alkylene oxide containing at least 3 carbon atoms.

This concept has been disclosed in U.S. Pat. No. 2,677,700. In accordance with a preferred embodiment of the invention of this patent, the lipophilic sequence is a polyoxypropylene chain and the hydrophilic sequence is a polyoxyethylene chain.

According to U.S. Pat. No. 3,454,646, the polyoxyethylenated chain is replaced by a sequence of (dialkyl amino-methyl)ethyleneoxy or (N-oxydialkyl amino methyl)ethylene oxy groups; the lipophilic sequence being obtained by the reaction of a lower alkylene oxide with a monoalcohol or a polyol.

It is also generally known that the surface activity of an amphiphile compound increases with the length of the lipophile chain, as evidenced, for instance in the disclosure of T. Kuwamura (Kobunshi Kogaku 17 p. 175-182, 1960) where it is shown that this rule is confirmed in the case of sequenced copolymers of alkyl glycidyl ethers and ethylene oxide.

Up to now it has not been possible to obtain polyethers with a sequenced structure having, simultaneously, both high surface activity and satisfactory water solubility characteristics.

The present invention now provides products which possess a combination of advantageous properties, i.e. surface activity, affinity for water, chemical stability and weak mucous aggressiveness.

This latter feature is particularly distinct and at the same time quite unexpected in the case of the compounds of the present invention for which B represents dialkyl amino groups or trialkyl ammonium salts, when compared to known cationic or quaternary surface active compounds.

The present invention thus relates to sequenced oligomer surfactants of the formulas L—Hy or Hy—L—Hy, which possess good surface active properties, a good affinity for water and a very weak aggressiveness vis-a-vis the skin and particularly ocular mucous.

Sequence L represents a succession of m units, (3a) or (3b):

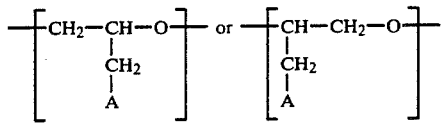

which can schematically be written as $-[C_2H_3(CH_2A)O]-$ (3) wherein A represents R—$CH_2$— or R'—O—; R being linear alkyl, with an even or odd number of carbon atoms from $C_4$ to $C_{16}$, preferably from $C_7$ to $C_{15}$ and advantageously from $C_{12}$ to $C_{15}$, and R' representing linear or branched alkyl, having an even or odd number of carbon atoms from $C_4$ to $C_{20}$, preferably from $C_8$ to $C_{14}$, and advantageously $C_{12}$; and m represents a whole or decimal number from 2 to 10 and advantageously from 2 to 6.

The Hy sequence represents a succession of n or n' units, (4a) or (4b), below; n and n' representing whole or decimal numbers from 2 to 25, with one of n and n' also being able to be zero:

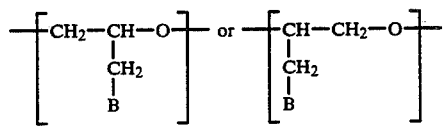

These isomeric forms can be schematically written as $$-[C_2H_3(CH_2B)O]- \qquad (4)$$

wherein
B represents

—OH,     (i)

(ii)

(iii)

(iv)

(v)

(vi)

wherein
$R_1$ and $R_2$ each independently represent alkyl having 1–3 carbon atoms, hydroxyalkyl having 1–3 carbon atoms or together with the adjacent nitrogen atom form a heterocycle having 5 or 6 chains and preferably piperidino or morpholino;

$R_3$ represents methyl or ethyl;

Z represents an anion and preferably $HSO_3^\ominus$, $CH_3SO_3^\ominus$, $CH_3SO_4^\ominus$, $CH_3-C_6H_4-SO_3^\ominus$;

$R_1R_2N^\oplus HV^\ominus$ and $R_1R_2N-O^\oplus HV^\ominus$ represent salts of amines and amine oxides, and preferably a hydrochloride, hydrobromide, sulfate, phosphate, acetate, lactate and tartrate wherein $R_1$ and $R_2$ have the meanings given above.

In another embodiment of the present invention, when the sequenced oligomer surfactant is employed in a cosmetic or pharmaceutical composition, B can also have the value:

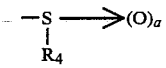

wherein a represents 0 or 1, and $R_4$ represents alkyl having 1–3 carbon atoms, hydroxyalkyl having 1–3 carbon atoms or dihydroxyalkyl having 2–3 carbon atoms, and preferably a methyl, ethyl, hydroxyethyl or dihydroxypropyl group. In a remotely general fashion, sulfur containing materials of this type are discussed in U.S. Pat. Nos. 3,576,906 and 3,821,306.

The new sequenced oligomer surfactants of the present invention can be represented by the following formula:

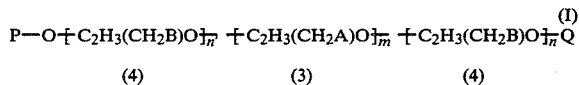

wherein units [C2H3(CH2B)O] and [C2H3(CH2A)O] can each be present under both isomeric forms (3a) and (3b) and (4a) and (4b), respectively, as indicated above.

When one of n or n' represents zero or when both are different from zero, the resulting oligomers are respectively of the type; L—Hy (1) or Hy—L—Hy (2).

In formula (I) above, A, B, m, n' and n have the same meaning given above and one of P and Q represents a hydrogen atom and the other represents a linear or branched alkyl having from 1–20 carbon atoms.

The process of producing a mixture of trisequenced oligomer surfactants of the Hy—L—Hy type (2) having formula (I) comprises the steps of:

(1) in a first stage telomerizing n' or n moles of epihalohydrin, such as epichlorohydrin or epibromohydrin, or of tertio butyl glycidyl ether on a POH or QOH alcohol, P and Q represents an alkyl radical having 1–20 carbon atoms, to produce a precursor of a first hydrophilic sequence;

(2) in a second stage telomerizing m moles of a straight chain epoxy alkane having 8–20 carbon atoms, a mixture of said epoxy alkanes, a straight or branched chain alkyl glycidyl ether having from 7–23 carbon atoms or a mixture of said alkyl glycidyl ethers, on said first hydrophilic sequence prepared in said first stage to produce a lipophilic sequence;

(3) in a third stage telomerizing n or n' moles of epihalohydrin such as epichlorohydrin or epibromohydrin, or of tertio butyl glycidyl ether on the lipophilic sequence prepared in said second stage to produce a precursor of a second hydrophilic sequence and (4) in a fourth stage replacing in the precursor of the first and second hydrophilic sequence prepared in the first and third stage (i) the tertio butyl groups by —OH groups or (ii) the halogen atoms by hydrophilic groups selected from —OH, $R_1R_2N-$, $R_1R_2N\rightarrow O$, $R_1R_2N\rightarrow O^\oplus HV^\ominus$, $R_1R_2N^\oplus HV^\ominus$, $R_1R_2N^{\ominus L}$ $^{N.V\ominus}$, $R_1R_2R_3N^\oplus Z^\ominus$ and $R_4S\rightarrow(O)a$, wherein $R_1$, $R_2$, $R_3$, $R_4$, a, $Z^\ominus$, $R_1R_2N^\oplus N.V^\ominus$ have the meanings given above.

The process of producing a mixture of bi-sequenced oligomer surfactants of the type L—Hy(1) having formula (II),

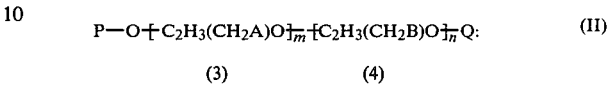

comprises the steps of (1) in a first stage telomerizing m moles of an epoxy alkane having a straight chain and having 8–20 carbon atoms, a mixture of said epoxy alkanes, an alkyl glycidyl ether having 7–23 carbon atoms or a mixture of said alkyl glycidyl ethers on a POH alcohol wherein P is a linear or branched alkyl having from 1–20 carbon atoms to produce a lipophilic sequence;

(2) in a second stage telomerizing n moles of epihalohydrin such as epichlorohydrin or epibromohydrin, or of tertio butyl glycidyl ether on a telomer, i.e. the lipophilic sequence prepared in said first stage to produce a hydrophilic sequence precursor; and (3) in a third stage replacing in the telomer i.e. the hydrophilic sequence precursor prepared in the second stage, (i) the tertio butyl groups by OH groups or (ii) the halogen atoms by hydrophilic groups selected from —OH, $R_1R_2N-$, $R_1R_2N\rightarrow O$, $R_1R_2N\rightarrow O^\oplus.V^\ominus$, $R_1R_2N^\oplus H.V^\ominus$, $R_1R_2R_3N^\oplus Z^\ominus$, or $R_4S\rightarrow(O)a$, wherein P, Q, A, B, $R_1$, $R_2$, $R_3$, a, $Z^\ominus$, $R_1R_2N^\oplus N.V^\ominus$ and $R_1R_2N\rightarrow O^\oplus H.V^\ominus$ have the meanings given above.

However, it is also possible to reverse the first and second stages described above and to prepare initially the polyhalogenated or polytertiobutylated telomer from a QOH alcohol where Q represents an alkyl radical having from 1–20 carbon atoms, which will give the hydrophilic sequence on which is condensed the lipophilic sequence.

The hydrophilic sequence Hy is obtained by telomerization of an epihalohydrin on a telogen containing an active hydrogen atom, the halogen then being replaced by a hydrophilic group or again by telomerization of the tertio butyl glydicyl ether and hydrolysis of the tertio butoxy group.

By telomerization is meant the reaction of an epoxide with a compound having an active hydrogen atom. The compound having an active hydrogen is called a telogen; the epoxide compound is called taxogen; and the product of the reaction is the telomer.

The compound with an active hydrogen, referred to above, can be an alcohol having 1–20 carbon atoms, or a telomer obtained from the reaction of such an alcohol and one or two monomers having an epoxide group such as an epoxy alkane, alkyl glycidyl ether or epihalohydrin.

Preferably, the lipophilic epoxide is telomerized initially, followed by telomerization of the epihalohydrin to produce compounds of the L—Hy type (1). On the other hand, to produce the compounds of the Hy—L—Hy type (2), the epihalohydrin is telomerized, then the lipophilic epoxide, followed lastly by telomerization again of the epihalohydrin.

The halogen substitution reaction is always carried out after the telomerization reactions.

When B in the Hy sequence represents OH, this sequence can be prepared (1) by telomerization of an epihalohydrin with a compound having an active hydrogen, followed by hydrolysis of the halogenated compound or (2) by telomerization of tertio butyl glycidyl ether, followed by a hydrolysis reaction during the course of which the tertio butyl group is replaced by the OH group.

In formulas (I) and (II), m, n and n' represent statistical average values and express the number of molecules having an epoxide function employed per molecule of compound having an active hydrogen, i.e. POH or QOH.

These latter compounds are selected from the class of saturated, linear or branched primary alcohols having 1–20 carbon atoms.

Preferably, there are employed alcohols which have a structure and a carbon atom content close to the alkyl group attached to the oxirane group of the monomer employed for the preparation of the lipophilic sequence.

For example 2-ethyl hexanol is employed as the telogen for the condensation of 2-ethyl hexyl glycidyl ether; decanol or dodecanol is used for the condensation of 1,2 epoxy dodecene; methanol or ethanol is used for the condensation of epihalohydrin.

For the preparation of the lipophilic sequence L, useful monomers having an epoxide function have the formula:

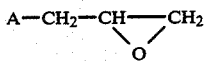
(5)

wherein A represents an alkyl or alkoxy group as defined above, that is compound (5) can be an epoxy alkane or an alkyl glycidyl ether.

Representative 1,2-epoxy alkanes usefully employed in the present invention include 1,2-epoxy-octane, -decane, -undecane, -dodecane, -tridecane, -tetradecane, -pentadecane, -hexadecane, -heptadecane, -octadecane, -eicosane, or a mixture thereof. Further commercial mixtures such as: (1) a mixture of $C_{11}$–$C_{14}$ epoxides sold under the mark "Nedox 1114", (2) a mixture of $C_{15}$–$C_{18}$ epoxides sold under the mark "Nedox 1518" or (3) a mixture of $C_{14}$–$C_{16}$ epoxides sold under the mark "Epoxyde 16" can also be used.

Representative alkyl glycidyl ethers usefully employed in the present invention include the derivatives of butyl, terio butyl, amyl, isoamyl, 2-ethyl hexyl, octyl, isooctyl, decyl, undecyl, dodecyl, tetradecyl, hexadecyl, 2-hexyl decyl, octadecyl, eicosyl, and 2-octyl dodecyl alcohols, natural or synthetic, or mixtures of these alcohols, or even commercial mixtures of alcohols, such as "Dobanol 25" obtained by the oxo process.

"Dobanol 25" represents a mixture of synthetic $C_{12}$–$C_{15}$ aliphatic alcohols, having straight and branched chains of which about 14% is 2-methyl alkanols.

Further commercial mixtures of glycidyl ethers such as $C_8$ and $C_{10}$ glycidyl ethers, $C_{11}$ and $C_{13}$ glycidyl ethers sold under the mark "Epoxyde 7", $C_{12}$–$C_{14}$ glycidyl ethers and $C_{15}$–$C_{17}$ glycidyl ethers sold under the mark "Epoxyde 8" can also be used.

The average degree of polymerization m of the lipophilic sequence is generally between 2 and 10 inclusive, preferably between 3 and 8 inclusive, and advantageously between 3 and 6 inclusive.

The hydrophilic sequences Hy of formula (4) are obtained respectively by telomerization of n or n' moles of epihalohydrin, such as epichlorohydrin or epibromohydrin, on a compound having an active hydrogen which is either an alcohol of the formula POH or QOH, or a telomer obtained from the reaction of a POH or QOH alcohol with an epoxyalkane and/or an alkylglycidyl ether. The telomerization reaction is followed by the replacement of the halogen substituents by hydroxy, N,N-dialkylamino, N,N-alkylhydroxyalkylamino, N,N-dihydroxyalkylamino, morpholino, piperidino, trialkylammonium, dialkylhydroxy alkylammonium, alkyldihydroxyalkyl ammonium, dialkylamino oxide, alkyloxide, hydroxyalkylamino, dihydroxyalkylamino oxide, alkyl thio, hydroxyalkyl thio, dihydroxyalkyl thio, alkyl sulfinyl, hydroxylalkyl sulfinyl and dihydroxyalkylsulfinyl. In the above groups the alkyl radical contains preferably from 1–4 carbon atoms.

The telomerization reaction of an epihalohydrin and, preferably, epichlorohydrin or epibromohydrin, with a compound having an active hydrogen is effected in the presence of a Lewis acid catalyst and preferably in the presence of boron trifluoride, stannic chloride, or antimony pentachloride, at a temperature from 25°–160° C. and preferably from 60°–120° C. and advantageously from 60°–75° C. by using the catalyst in an amount of 0.1 to 3 weight percent, preferably 0.2 to 1.5 weight percent, relative to the total reaction mass.

The polyhalogenated polymers obtained are preferably washed with water and neutralized with sodium hydroxide or potassium hydroxide. The volatile products that they may optionally contain are removed by molecular distillation at a temperature of 150°–220° C. under reduced pressure in the order of $10^{-3}$ mm Hg.

The polyhalogenated telomers according to the invention have a molecular weight between 700 and 5,000 and more generally between 900 and 3,000.

When the halogen is replaced by an OH group a hydrophilic unit of the following formula is obtained:

(6)

which corresponds to the following two isomers:

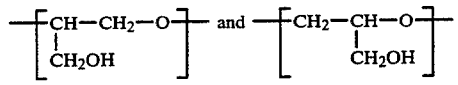

(6a)   (6b)

This substitution is carried out by heating the polyhalogenated telomer with an alkaline salt of a carboxylic acid and preferably with sodium or potassium acetate in a solvent which assures both the miscibility of the reactants and easy separation of the alkaline halide formed. The alkaline acetate is used in stoichiometric amounts or in slight excess relative to the halogenated compounds. Moreover, there is also obtained in addition to the alkaline halide, an acetic ester that is separated from the halide formed. The acetic ester is then decomposed (1) by hydrolysis, (2) alcoholysis or (3) saponification, to obtain the hydroxyl unit (6). Representative solvents which are conveniently employed for the hydroxylation reaction, include glycols, and preferably ethylene glycol, butylene glycol, diethylene glycol and their ethers; propylene glycol; dipropylene glycol; hexylene glycol; and 2-butoxy ethanol, the boiling points of which are sufficiently high to avoid use of an autoclave. The amount of solvent employed during the course of the hydroxylation phase is at least 50% by weight of polyhalogenated ether being hydroxylated, and preferably from 100 to 400% of this weight.

The reaction is carried out at a temperature between 150° and 200° C. and preferably at a temperature of 180°–190° C. The addition of a reducing agent, such as sodium hypophosphite or alkaline borohydride, to the hydroxylation reaction avoids coloration of the products obtained.

It is possible to regenerate the acetates "in situ" from esters formed during the course of the reaction, for example, by the addition of an aqueous solution of an alkaline hydroxide with instantaneous evaporation of the water.

The reaction lasts about 6 hours, the rate of transformation being greater than 90%, and generally greater than 95%.

The acetic ester is saponified with sodium or potassium hydroxide or it is subjected to alcoholysis with anhydrous methanol or ethanol, in the presence of a catalyst which is advantageously sodium or potassium methylate or ethylate. The replacement of the halogen atoms by OH groups is described in greater detail in commonly owned French Pat. No. 1,477,048 or U.S. Pat. No. 3,578,719.

The unit (6) can also be obtained by replacing the epihalohydrin with the tertio butyl glycidyl ether, the latter being telomerized with a compound having an active hydrogen atom, as defined above. There are thus obtained polyethers having oxyalkylene units and being of the formula:

which corresponds to the following two isomers:

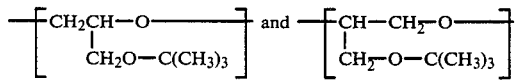

(7a)        (7b)

Hydrolysis of the protective tertio butyl group and its replacement by hydroxyl groups is carried out in the presence of water and a strong acid catalyst which is, preferably, a sulfocarboxylic acid, at a temperature of 80°–110° C. and preferably, 100°–105° C.

The reaction of the tertio butyl glycidyl ether with the compound having an active hydrogen is effected in the presence of an acid catalyst such as Lewis acids and, in particular, boron trifluoride, stannic tetrachloride or antimony pentachloride, in an amount of 0.1 to 3 percent and preferably, 0.2 to 1.5 percent, by weight relative to the total weight of the reaction mixture. The reaction is carried out preferably at a temperature of 60° to 90° C.

Representative sulfocarboxylic acids used as catalysts in the second stage, wherein the tertio butyl group is cleaved, include aromatic sulfonic acids, such as benzene sulfonic acid, paratoluene sulfonic acid and sulfo salicylic acid; aliphatic sulfonic acids having a hydroxyl group, such as the hydroxyalkane sulfonic acids, for example 3-hydroxypropane sulfonic acid; the sulfocarboxylic acids and their esters, in particular, α-sulfonated carboxylic acids such as α-sulfoacetic acid, α-sulfo lauric acid, α-sulfo palmitic acid, α-sulfo stearic acid as well as the esters of these acids and lower alcohols containing 1–4 carbon atoms.

These catalysts are used in an amount of 0.2 to 10 percent by weight and preferably, 0.5 to 5 percent by weight relative to the tertiobutyl polyether, these amounts being calculated on the basis of pure anhydrous catalysts. To obtain the hydrolysis of the tertio butyl group there is employed an amount of water ranging from 0 to 200 percent by weight relative to the polyether.

In accordance with a preferred embodiment, the polyether is heated while agitating it, to which initially there is introduced the catalyst and subsequently to which there is added the water in a progressive manner. It is important not to introduce the catalyst in the form of a dilute aqueous solution. However, crystallized hydrates or aqueous solutions containing 50 weight percent of these catalysts can be used. The hydrolysis can also be carried out in a hydroalcoholic medium, for example in water-ethanol or water-tertiary butyl alcohol mixtures. At the end of the reaction, the catalyst is removed either by precipitation under the form of insoluble salts, followed by a separation by filtration, or by passing the reaction mixture over a basic ion exchange resin. When as the catalyst, there is used a sulfo-carboxylic acid, this latter can partially esterify the polyhydroxylated polyethers formed during the course of hydrolysis and this without any inconvenience to the completion of this reaction. Thus, at the end of the reaction, these esters of sulfocarboxylic acids and polyhydroxylated polyethers can be saponified.

The compounds thus prepared have the hydrophilic unit, ${C_2H_3(CH_2OH)O}$ (6) and they are nonionic surface active agents.

In the hydrophilic unit, ${C_2H_3(CH_2B)O}$ (4), B can also represent a dialkyl nitrogen which can be oxidized and which is capable of being positively charged by salification with a mineral or organic acid or even by quaternization with a currently employed alkylation agent, thus providing cationic surface active agents.

These cationic surface active agents are prepared by heating the polyhalogenated telomer with a secondary amine or with a tertiary amine, for several hours, for example from 1–10 hours, between 80° and 180° C. and preferably at a temperature from 120°–160° C., under a nitrogen atmosphere, at atmospheric pressure or in an autoclave.

Optionally an inert solvent can be used if the medium is heterogeneous or if the viscosity is too high.

There is thus obtained, depending on the choice of reactant, a tertiary polyamine or a quaternary polyammonium.

Representative amines which can be used include: dimethylamine, diethylamine, dipropylamine, methylethanol amine, ethyl ethanolamine, diethanolamine, piperidine, morpholine, trimethylamine, dimethyl ethanolamine, or a mixture thereof.

When the substitution has been effected with a tertiary amine, the affinity for water of the surface active agent obtained can be increased by oxidation thereof to an amine oxide by means of $H_2O_2$ or a peracid such as performic acid or peracetic acid and/or salification with a mineral acid such as hydrochloric acid, sulfuric acid, phosphoric acid or by an organic acid such as acetic acid, lactic acid, tartaric acid or again by quaternization with a classic alkylation agent such as dimethyl sulfate, methyl methane sulfonate, methyl paratoluene sulfonate, glycol chlorhydrin and glycerol chlorhydrin.

In units, (4), B can also represent alkyl thio, hydroxyalkyl thio or dihydroxyalkyl thio groups and, preferably, hydroxyethyl thio, dihydroxypropyl thio, alkyl sulfinyl, hydroxyalkyl sulfinyl or dihydroxyalkyl sulfinyl, and preferably hydroxyethyl sulfinyl or dihydroxypropyl sulfinyl.

The halogen replacement reaction is then effected by heating the polyhalogenated telomer with 2-mercapto ethanol or thioglycerol, in the presence of sodium or potassium hydroxide, or sodium or potassium methylate or ethylate, as the acid acceptor and in the presence of a solvent such as ethanol, isopropanol, butanol, t-butanol, monomethyl ether of ethylene glycol (methyl Cellosolve), or the monoethyl ether of ethylene glycol (ethyl Cellosolve), at a temperature of 60°–130° C. and, preferably, at the solvent reflux temperature.

Also water can optionally be added to partially or totally solubilize the sodium halide formed and the reaction can be carried out in an autoclave in the case of gaseous or very volatile compounds.

The rate of reaction generally is greater than 90% and often it is greater than 95%.

The polyethers thus obtained, which are part of the compounds of the present invention can be soluble or dispersible in water depending, for instance on ratio $(n+n')/m$ and on the nature of the thioalkyl group which replaces the halogen atom.

The hydrophilic characteristic of these compounds can be significantly increased by oxidizing the thioether groups to sulfoxide groups. In accordance with a classic procedure, the compounds are oxidized with $H_2O_2$, at about 39% by weight, (130 volumes), in the presence, optionally, of a catalytic amount of acetic acid, at a temperature between 20° and 50° C., and preferably 30°–35° C.

It is clear that during the course of the telomerization reactions a mixture of compounds is formed for which the number of fixed molecules, respectively of epihalohydrin, tertiobutyl glycidyl ether, epoxy alkane or alkyl glycidyl ether, can be higher or lower than n′, m or n (the number of moles of compound with epoxide function that are reacted with the alcohol or on the telomer containing an active hydrogen atom). From this it results that there is obtained a mixture of bisequenced or trisequenced compounds of formula (I) in which the combined values of n′, m and n (in the trisequenced oligomers) or m and n (in the bisequenced oligomers) are distributed statistically about an average value corresponding to the number of moles of the compound with the epoxide function employed in the different stages of the reaction.

Thus, the process of the present invention makes it possible to regulate at will the hydrophilic and lipophilic character of the bi- and tri-sequenced oligomers, by simply selecting various values for m, n and n′, as well as A and B.

The sequenced oligomers prepared in accordance with the process of the present invention have a molecular weight ranging between 500 and 5,000, and more generally between 800 and 3,000.

The L—Hy and Hy—L—Hy oligomers are generally dispersible or soluble in water when the ratio of $(n+n')/m$ ranges from 2 to 10 and preferably from 4 to 10.

The solubility of these oligomers will be the greater as this ratio is great. The water solubility of these oligomers also depends on the nature of the A and B groups. It diminishes when the number of carbon atoms of A increases and when the solubilizing power of B diminishes, and inversely.

The water solubility of these oligomers is only slightly affected by the presence of electrolytes such as sodium chloride or NaOH or by raising the temperature thereof.

The oligomers of the present invention include in their hydrophilic sequence some hydroxyl, amine or thio ether groups which are furthermore reactive sites on which it is possible to effect various chemical reactions such as a condensation, a telomerization or an alkylation reaction.

The compounds of formula (I) have good surface activity, and their amphipatic properties (lipophilic and hydrophilic) can be modified at will by varying the A and B groups and the degrees of polymerization, m, n and n′.

These oligomers can be used as weak foaming agents, wetting agents, detergents, emulsifying agents, peptizing agents, dispersants, softening agents, anti-clogging agents, solubilization agents, penetrating agents, anti-redeposition agents, flotation agents, anti-static finishing agents or a dye auxiliary.

Generally, the chemical stability of these compounds imposes practically no limitation on their use.

Their molecular weight and their weak aggressiveness make them particularly desirable in the field of capillary compositions, cosmetic or pharmaceutical, for example, as additives for shampoos, as carriers for hair dye compositions or as excipients.

The oligomers of the present invention can, in these compositions, be used as surfactants alone, or in admixture with other compounds of the anionic, cationic, nonionic or amphoteric type.

The invention also relates to halogenated compounds of the formula:

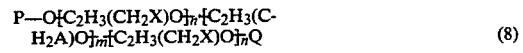 (8)

wherein
$\{C_2H_3(CH_2X)O\}$ represents the two isomers:

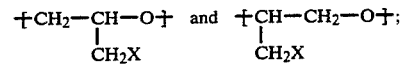

$\{C_2H_3(CH_2A)\}$ represents the two isomers:

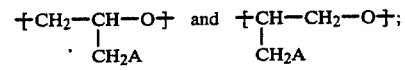

P, Q, A, m, n and n′ have the meanings given above for formula (I); and X represents chlorine or bromine.

The present invention further relates to polytertiobutoxy compounds of the formula:

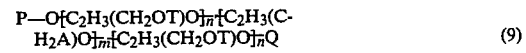 (9)

wherein
$\{C_2H_3(CH_2OT)O\}$ represents the two isomers:

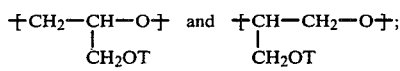

─{C₂H₃(CH₂A)O}─ represents the two isomers:

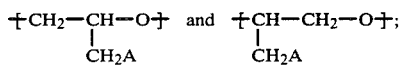

T represents the tertio butyl group,

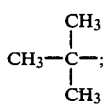

and

P, Q, A, m, n' and n have the meanings given above for formula (I).

The present invention also relates to compositions containing as the principal surfactant or as an additive, at least one sequenced oligomer of formula (I).

The compounds of formula (I) are used in these compositions in an amount from 0.1–80 weight percent, advantageously from 0.5–40 weight percent and preferably from 1–15 weight percent based on the total weight of the composition.

The compositions contemplated are pharmaceutical or cosmetic compositions and preferably capillary compositions, compositions used for the treatment of natural or synthetic textiles and compositions used for the treatment of leather, minerals, metals and heavy oils.

The reason that the compounds of the present invention are used in capillary compositions, cosmetic or pharmaceutical, resides principally in their great surface activity, their weak aggressiveness and their good affinity for water despite their molecular weight. The pH of these compositions is between 3 and 12 and preferably between 4 and 10.

The present invention also relates to pharmaceutical compositions including, as an excipient, at least one polyhydroxylated, sequence oligomer surfactant of formula (I).

Moreover, the present invention also relates to cosmetic compositions including at least one compound of formula (I). The cosmetic compositions include principally those for use in the care of the skin, nails and hair.

The compositions for use in the care of the hair are principally compositions for washing the hair, notably hair shampoos, as well as hair conditioning compositions and hair dye compositions. These latter also include one or more dyes, principally oxidation dyes (with or without couplers and with an oxidizing agent such as, preferably H₂O₂). The dye composition can also include leucoderivatives of indamines, indoanilines and indophenols as well as direct dyes such as, principally, azo dyes, anthraquinone dyes, nitrobenzene dyes, indamines, indoanilines and indophenols.

The shampoo compositions can include in addition to the sequenced oligomer surfactant of this invention one or more amphoteric or nonionic surfactants as well as other cosmetic adjuvants.

The cosmetic compositions are provided in the form of an aqueous or hydroalcoholic solution, or in the form of a cream, a gel, an emulsion or an aerosol.

The hydroalcoholic solutions include, generally, an alcohol having 1–4 carbon atoms and preferably ethanol or isopropanol, in an amount from 5 to 70 percent by weight based on the total weight of the composition.

The cosmetic and pharmaceutical compositions can include the compounds of formula (I) in amounts ranging from 0.1 to 80 weight percent, advantageously from 0.5 to 40 weight percent and preferably from 1 to 15 weight percent, based on the total weight of the composition.

The compound of formula (I) can be used in these compositions as the only surfactant or in admixture with other surfactants of the anionic, cationic, nonionic or amphoteric type.

The compositions can also include acids or bases, foam synergists, foam stabilizers, thickening agents, opacifiers, sequesterants, super-fatting agents, antiseptics, preservatives, treating products, cosmetic polymers, pigments, perfumes, dyes, dye solvents, solar filters, oxidizing agents and all adjuvants conventionally employed in cosmetic compositions which comprise capillary compositions.

The acids and bases are used in an amount sufficient to adjust the pH of the composition to between 3 and 12 and preferably between 4 and 10.

Representative thickening agents usefully employed include, principally, cellulosic derivatives such as carboxymethyl cellulose, hydroxypropylmethyl cellulose, hydroxyethyl cellulose and acrylic polymers. The thickening agents are generally employed in an amount from 1 to 20 percent by weight based on the total weight of the composition.

Representative polymers usefully employed include various cationic, anionic and nonionic polymers generally employed in cosmetic compositions, such as the polymers and copolymers of vinyl pyrrolidine and ethylene imine.

These polymers are generally used in an amount from 1 to 3 weight percent based on the total weight and the composition.

Representative solvents usefully employed include the glycols, for example, ethylene glycol, propylene glycol, butyl glycol, diethylene glycol and the monoethyl ether of diethylene glycol. The glycols are employed, generally, in an amount between 0.5 and 10 weight percent, preferably between 1 and 6 weight percent, based on the total weight of the composition.

The following non-limiting examples are given to illustrate the invention. Unless otherwise stated all parts and percentages are by weight.

Examples of Oligomer Preparation

EXAMPLE 1A

Preparation of a polyhalogenated bisequenced oligomer intermediate of the formula

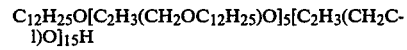

To 18.6 g of dodecanol (0.1 mole), sold under the mark "ALFOL 12", these are added, over a period of 1½ hours, at a temperature of 75° C.±5° C., alternately in 3 fractions, 2.16 ml of SnCl₄ and 125 g (0.5 mole) of dodecyl glycidyl ether. The temperature and agitation of the reaction mixture are maintained for 2 hours. One checks by dosage that all the epoxide has been consumed. There are then added alternately and in 3 equal fractions and always at 75° C.±5° C., 1.4 ml of SnCl$_4$ and 138 g (1.5 moles) of epichlorohydrin. The addition lasts for 1½ hours.

After 2 hours of agitation at 75° C., the reaction is practically complete; no longer is there detected by dosage any epoxide groups.

The product thus obtained is clear and has a pale yellow color. The product is washed three times with 500 ml of boiling water and dehydrated by heating it under reduced pressure.

The molecular weight of the product, measured by the lowering vapor tension method, is 1,000. After removal of the volatile materials (10%), by molecular distillation at a temperature of 210° C., the molecular weight of the product is 1,475. Its hydroxyl index is 0.65 meq/g (milliequivalent per gram) and its organic chloride index is 5.3 meq/g.

EXAMPLE 1B

Preparation of a cationic bisequenced oligomer of the formula:

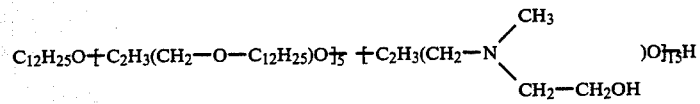

To 40 g (212 meq) of the polyhalogenated derivative of Example 1A, there are added 42.5 g (530 meq) of methylethanolamine, sold under the mark "AMIETOL M 11". The mixture is heated to 130° C. under a nitrogen atmosphere for a period of 2½ hours. The rate of reaction calculated from the acid index is 99%. The acidity formed is then neutralized with 21.5 g of NaOH at 9.84 meq/g after having dissolved the product in 120 ml of isopropanol. The resulting sodium chloride is filtered on fritted glass and the isopropanol is distilled. Excess amine is removed by heating under reduced pressure.

The product thus obtained is provided in the form of a very thick brown oil, nearly completely soluble in water.

On the addition of a small amount of a mineral or organic acid, the solution completely clarifies. Base Index: 4.17 meq/g.

EXAMPLE 1C

Preparation of a non-ionic bisequenced oligomer of the formula

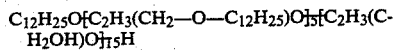

To 137 g of the polyhalogenated derivative of Example 1A (767 meq of Cl), there are added 137 g of diethylene glycol and then 78 g of potassium acetate (805 meq).

The mixture is heated for a period of 5½ hours at 185° C. under a nitrogen atmosphere. The reaction rate is determined by dosage of the basicity remaining and the chloride ions formed. The reaction rate thus calculated is 97%.

The resulting potassium chloride is filtered on fritted glass and the diethylene glycol is removed by heating at 180°–185° C. under reduced pressure.

The resulting product is then subjected to alcoholysis by adding 130 ml of absolute ethanol and 1.19 g of sodium methylate. This mixture is then left to stand at ambient temperature for 12 hours. Thereafter the mixture is filtered and the ethanol is removed under reduced pressure.

The expected product is provided in the form of a brown paste, dispersible in water. Its cloud point as a 0.5% solution thereof in a 25% solution of butylglycol in water is 85° C. Hydroxyl Index: 5.95 meq/g.

EXAMPLE 1D

Preparation of a polysulfoxide nonionic bisequenced oligomer of the formula

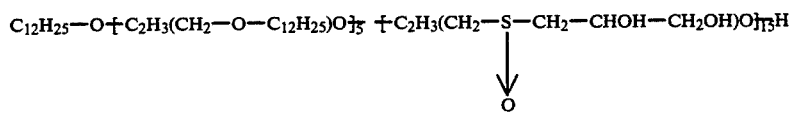

To 40 g of the polyhalogenated derivative prepared in Example 1A (212 meq), there are added, under a nitrogen atmosphere, 26 g of thioglycerol (212 meq) and then 30 ml of absolute ethanol. The mixture is then heated to 65° C. at which point there are slowly added 21.2 g of NaOH (10 meq/g). The mixture is then heated at reflux for 5 hours.

The reaction rate is determined by dosage of the alkalinity and the remaining mercaptans.

There are then added 300 ml of absolute ethanol and the mixture is filtered to remove the sodium chloride.

The ethanol is then removed by heating under reduced pressure. To 50 g of the polythioether thus obtained, there is added 0.5 ml of acetic acid and then at 35° C., there are slowly added 16.6 ml of H$_2$O$_2$ at a concentration of about 39% by weight (130 volumes) under strong agitation.

Thereafter about 30 ml of water are added to fluidify the reaction mass.

There is thus obtained a very thick transparent product having a pale yellow color and exhibiting slight opalescence in water. Its cloud point in water at a concentration of 5% is greater than 100° C.

EXAMPLE 2A

Preparation of a polyhalogenated bisequenced oligomer intermediate of the formula

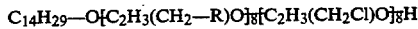

wherein R is a mixture of C$_{11}$ and C$_{13}$ alkyls.

To 21.4 g of tetradecanol, sold under the mark "ALFOL 14" (0.1 mole), there are added, over a two hour period, at a temperature of 70° C., alternately in two equal fractions, 1.1 ml of SbCl$_5$ and 190 g (0.8 mole) of a mixture of 1,2-epoxy tetradecane and 1,2-epoxy hexadecane, approximately in the proportions 2.72:1, sold under the mark "EPOXYDE 16".

This temperature and agitation are maintained for 1 hour.

One checks by dosage that all the epoxide has been consumed. Hydroxyl Index: 0.65 meq/g.

There are then added, alternately in two fractions, at 75° C., 0.37 ml of $SbCl_5$ and 74 g of epichlorohydrin (0.8 mole) over a 40 minute period. After 1 hour of agitation at 75° C., the reaction is practically complete.

The product thus obtained is washed three times with 500 ml of boiling water and then dehydrated by heating it under reduced pressure. The volatile materials (11%) are removed by molecular distillation at a temperature of 190° C.

The product obtained is provided in the form of a clear yellow oil having a molecular weight of 1,360.

Amount of organic chloride: 2.96 meq/g.

EXAMPLE 2B

Preparation of a cationic bisequenced oligomer of the formula

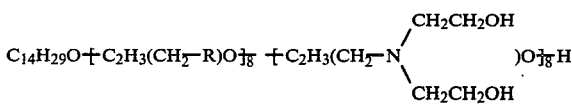

wherein R is a mixture of $C_{11}$ and $C_{13}$ alkyls.

To 80 g (224 meq) of the polyhalogenated derivative prepared in Example 2A, there are added, under a nitrogen atmosphere, 72 g of diethanolamine (672 meq). The mixture is heated at 130° C. with agitation for 8 hours. The reaction rate is 72%.

The reaction mixture is then re-heated for 4 hours at 150° C.; the reaction is then practically complete.

The product obtained is washed three times with 400 ml of boiling water and then dehydrated by heating it under reduced pressure.

The product obtained is provided in the form of a thick oil having a light chestnut color. The product gives, in water, a slightly cloudy solution. This cloudiness disappears by the addition of a small amount of a mineral or organic acid.

Base Index: 1.96 meq/g.

EXAMPLE 2C

Preparation of an amine oxide bisequenced oligomer of the formula

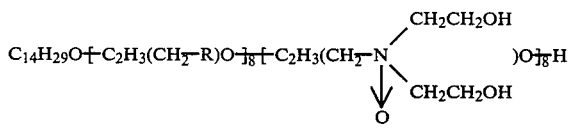

where R is a mixture of $C_{11}$ and $C_{13}$ alkyls.

To 25 g (63 meq) of the cationic derivative prepared in Example 2B, there are added, at 45° C., over a 25 minute period, 5.4 ml of $H_2O_2$ (about 39 weight percent, or 130 volumes—63 meq).

The product obtained is provided in the form of a whitish soft paste. The product is soluble in water with slight opalescence which disappears if a little mineral or organic acid is added thereto.

EXAMPLE 2D

Preparation of a nonionic bisequenced oligomer of the formula

wherein R is a mixture of $C_{11}$ and $C_{13}$ alkyls.

To 45 g of the polyhalogenated derivative prepared in Example 2A (135 meq of Cl), there are added, initially, 46 g of dipropylene glycol and then 15 g of potassium acetate (148 meq). The mixture is heated for 8 hours at 185° C. The reaction rate which is checked by dosage of the chloride ions and the remaining basicity is nearly 90%. The dispropylene glycol is removed by heating under reduced pressure.

The product is then subjected to alcoholysis by adding 50 ml of absolute ethanol and 0.4 g of sodium methylate (5.4 meq/g).

The resulting mixture is left to stand for about 12 hours at ambient temperature. Then the ethanol is removed by heating under reduced pressure. The product obtained is deep brown.

Hydroxyl Index: 3.85 meq/g.

EXAMPLE 3A

Preparation of a polyhalogenated bisequenced oligomer intermediate of the formula

wherein R is 2-ethyl hexyl.

To 19.5 of 2-ethyl hexanol (0.15 mole) there are added, at 65° C.±5° C., alternately, in two fractions and over a period of 2 hours and 40 minutes, 1.5 ml of $SbCl_5$ and 294 g of 2-ethyl hexyl glycidyl ether (1.5 moles).

Hydroxyl Index: 0.91 meq/g

There are then added, alternately and in two fractions at 70° C., 1.5 ml of $SbCl_5$ and 276 g (3 moles) of epichlorohydrin. The addition lasts 2 hours.

The mixture is then left to stand for 2 hours at 70° C. with agitation. The reaction is at this point practically complete; no longer is there detected by dosage any epoxide groups.

The resulting product is washed three times with 1 liter of boiling water and then dehydrated by heating it under reduced pressure.

The molecular weight of the product obtained is 1,280. After removal by molecular distillation at 225° C. of the volatile materials (about 11%), the molecular weight is 1,840.

Amount of organic chloride: 4.85 meq/g.

EXAMPLE 3B

Preparation of a cationic bisequenced oligomer of the formula

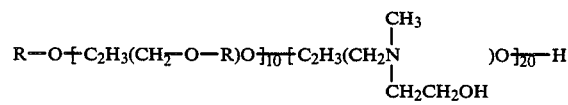

wherein R is 2-ethyl hexyl.

To 50 g of the polyhalogenated derivative prepared in Example 3A, there are added 51.3 g of methyl ethanolamine (636 meq), sold under the mark "AMIETOL M 11".

The mixture is heated with agitation and in a nitrogen atmosphere at 130° C. for 3 hours.

The rate of transformation of organic chloride is 99%.

The acidity is neutralized with 38.8 g of sodium methylate (5.8 meq/g). The reaction mixture is filtered and excess amine is removed by heating under reduced pressure.

The product obtained is a clear, viscous, reddish oil, soluble in water.

Its cloud point in a 0.5% solution in water is 64° C.

EXAMPLE 3C

Preparation of a polysulfoxide nonionic bisequenced oligomer of the formula

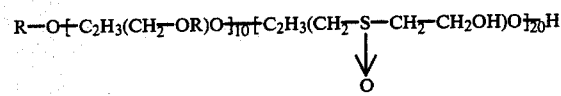

wherein R is 2-ethyl hexyl.

To 36.9 g of the polyhalogenated derivative prepared in Example 3A (179 meq/g), there are added, initially, under a nitrogen atmosphere, 14 g of 2-mercaptoethanol (179 meq/g) and then 20 ml of absolute ethanol.

The mixture is heated at 65° C. Then there are slowly added 17.9 g of NaOH (10 meq/g). This mixture is heated at reflux for 4 hours.

The reaction rate which is determined by dosage of the alkalinity and the remaining mercaptans, is 94%.

The product thus obtained is washed three times with 60 ml of boiling water and then dehydrated by heating it under reduced pressure. The product thus obtained has the appearance of a very thick amber colored oil, which is dispersible in water.

To 27 g of the polythioether thus obtained (96.4 meq), there is initially added 0.5 ml of acetic acid and then at 35° C., there are slowly added 8.3 ml of $H_2O_2$ at about 39 weight percent, or 130 volumes (96.4 meq), under strong agitation.

The product obtained is a light yellow paste, dispersible in water.

EXAMPLE 3D

Preparation of a polysulfoxide nonionic bisequenced oligomer of the formula

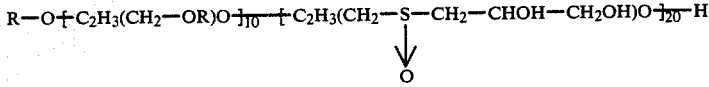

wherein R is 2-ethyl hexyl.

To 50 g of the polyhalogenated derivative prepared in Example 3A (242 meq/g), there are added under a nitrogen atmosphere, 29.4 g of thioglycerol (242 meq) and 20 ml of absolute ethanol. The mixture is heated at 65° C., and there are slowly added thereto 24.2 g of NaOH (10 meq/g). This mixture is heated at reflux for 4 hours.

The reaction rate, which is determined by dosage of the alkalinity and remaining mercaptans, is 93%.

There are then added 250 ml of absolute ethanol and the mixture is filtered on fritted glass to remove the sodium chloride. The ethanol is then removed by heating under reduced pressure.

To 55 g (199 meq) of the polythioether thus obtained, there is initially added 0.5 ml of acetic acid and then at 35° C., under strong agitation, there are added 17.1 ml of $H_2O_2$ at a concentration of about 39 weight percent or 130 volumes (199 meq).

About 5 ml of water are added to fluidify the reaction mass.

The product thus obtained is a very thick transparent oil, having a golden yellow color. It is very easily dispersible in water.

EXAMPLE 3E

Preparation of a polythioether nonionic bisequenced oligomer of the formula

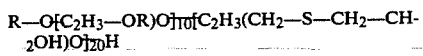

wherein R is 2-ethyl hexyl.

To 70 g of the polyhalogenated derivative prepared in Example 3A (340 meq/g), there are added under a nitrogen atmosphere, 27 g of mercaptoethanol (340 meq) and 30 ml of absolute ethanol.

The mixture is heated at 65° C. and 3.43 g of NaOH (9.9 meq/g) are slowly added thereto. The mixture is heated at reflux for 5 hours.

The reaction rate which is determined by dosage of the alkalinity and remaining mercaptans, is 97%.

After adding about 150 ml of absolute ethanol, the reaction mixture is filtered on fritted glass to remove the sodium chloride. The solvent is removed by heating under reduced pressure.

The product thus obtaned has the appearance of a very thick amber colored oil, dispersible in water.

Thioether Index: 4.25 meq/g.

EXAMPLE 4A

Preparation of a polyhalogenated bisequenced oligomer intermediate of the formula

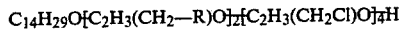

wherein R is a mixture of $C_{12}-C_{15}$ alkyls.

To 42.8 g of tetradecanol sold under the mark "ALFOL 14" (0.2 mole) there is initially added at a temperature of 65° C., 0.36 ml of $BF_3$ etherate. Then are added 101 g (400 meq) of a mixture of $C_{15}-C_{18}$ epoxy alkanes sold under the mark "NEDOX 1518" and containing the following % of epoxy alkanes: 1.5% $C_{14}$; 28% $C_{15}$; 28% $C_{16}$; 22.9% $C_{17}$; 19,6% $C_{18}$.

After 2 hours at 70° C., all the epoxide is consumed and the hydroxyl index of the product obtained is 1.54 meq/g.

0.18 ml of $BF_3$ etherate is added at 70° C. Then over a 35 minute period, 73.6 g of epichlorohydrin (0.8 mole) are added.

After 1½ hours of agitation at 70° C., the reaction is practically complete; no longer is there detected, by dosage, any epoxide groups. The product is washed three times with 400 ml of boiling water and then dehydrated by heating it under reduced pressure.

The product thus obtained is a light chestnut colored clear oil having a molecular weight of 810.

4,620,037

This temperature and agitation are maintained for 45 minutes.

One checks by dosage that all the epoxide has been consumed. There are then added, alternately in two fractions over a 50 minute period, at 70° C., 0.55 ml. of SbCl$_5$ and 111 g of epichlorohydrin (1,200 meq). After 2 hours of agitation at 75° C. the reaction is practically complete.

The product is washed three times with 500 ml of boiling water and dehydrated by heating it under reduced pressure. By molecular distillation at a temperature of 226° C., the most volatile materials (10%) are removed.

There is thus obtained a product having a molecular weight, measured by the lowering vapor tension method, of 1,330. The product is in the form of an amber colored oil.

Amount of organic chloride: 4.35 meq/g.

EXAMPLE 6B

Preparation of a cationic bisequenced oligomer of the formula

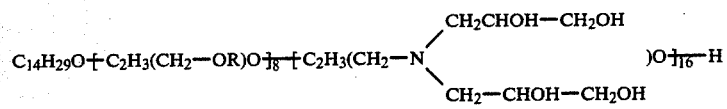

wherein R is a mixture of C$_{12}$ and C$_{14}$ alkyls.

To 60 g of the polyhalogenated derivative prepared in Example 6A (264 meq), there are added 94.6 g of di-isopropanolamine (720 meq).

The resulting mixture is heated, initially, under a nitrogen atmosphere for 14 hours at 140°–150° C. and then for 3 hours at 170° C. The reaction rate calculated from the acid index is 96%.

The product is washed three times with boiling water. After drying, the product is in the form of a deep yellow colored, very thick paste, which is soluble in water on the addition of a small amount of a mineral or organic acid.

Base Index: 2.7 meq/g.

EXAMPLE 6C

Preparation of a nonionic bisequenced oligomer of the formula

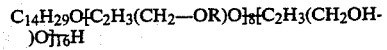

wherein R is a mixture of C$_{12}$ and C$_{14}$ alkyls.

To 60 g of the polyhalogenated derivative prepared in Example 6A (264 meq), there are added 60 g of dipropylene glycol and 23.8 g of sodium acetate. The mixture is heated for 7 hours at 185° C.

The reaction rate which is checked by the dosage of the remaining basicity and the chloride ions formed, is 93%.

The resulting product is then subjected to alcoholysis by adding thereto, with agitation, 60 ml of absolute ethanol and 0.52 g of sodium methylate (5.1 meq/g). This mixture is left to stand at ambient temperature for about 12 hours. The ethanol is then distilled under reduced pressure.

The product obtained has the appearance of a very deep colored thick oil which is dispersible in water.

Hydroxyl Index: 5.7 meq/g.

EXAMPLE 6D

Preparation of a quaternary ammonium bisequenced oligomer of the formula

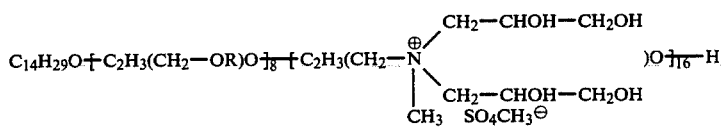

wherein R is a mixture of C$_{12}$ and C$_{14}$ alkyls.

To 43 g of the cationic derivative prepared in Example 6B (124 meq), there are added over a 40 minute period, at 50° C., 16.9 g of dimethyl sulfate (124 meq) and 10 g of methanol to fluidify the reaction mass.

This temperature and agitation are maintained for 3 hours.

The product obtained is provided in the form of a thick, beige colored paste which is soluble in water with a slight opalescence. Base Index: 0.3 meq/g.

EXAMPLE 7A

Preparation of a polyhalogenated bisequenced oligomer intermediate of the formula

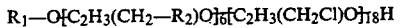

wherein R$_1$ is a mixture of C$_{12}$ and C$_{14}$ alkyls and R$_2$ is a mixture of C$_8$–C$_{11}$ alkyls.

To 9.7 g (50 meq) of a mixture of 55% dodecanol and 45% tetradecanol sold under the mark "ALFOL 1214", there are added over 1 hour period, at a temperature of 65° C., 0.37 ml of BF$_3$ etherate and 64 g (300 meq) of a mixture of C$_{11}$–C$_{14}$ epoxy alkanes sold under the mark "NEDOX 1114" having the following composition: 28.2% C$_{11}$ epoxyalkanes, 28.2% C$_{12}$ epoxy alkanes, 26.2% C$_{13}$ epoxyalkanes and 17.4% C$_{14}$ epoxy alkanes.

This temperature and the agitation are maintained for 45 minutes. One checks by dosage that all the epoxide has been consumed. There are then added at 65° C., over a 1 hour period and in three fractions, 0.58 ml of BF$_3$ etherate and 289 g of epichlorohydrin (900 meq).

This temperature and agitation are maintained for 2 hours. No longer is there detected by dosage any epoxide groups.

The hydroxyl index of the product obtained is 0.93 meq/g. The product is washed three times with 300 ml of boiling water and then dehydrated by heating it under reduced pressure.

By molecular distillation, at a temperature of 225° C., the most volatile products (about 11%) are removed.

The product thus obtained has a molecular weight of 1,200.

Organic chloride: 5.86 meq/g.
Hydroxyl Index: 0.8 meq/g.

EXAMPLE 7B

Preparation of a quaternary ammonium bisequenced oligomer of the formula

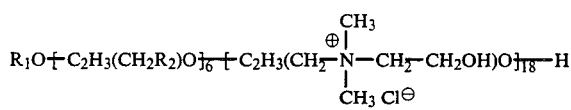

wherein $R_1$ is a mixture of $C_{12}$ and $C_{14}$ alkyls and $R_2$ is a mixture of $C_8$–$C_{11}$ alkyls.

To 50 g of the polyhalogenated derivative prepared in Example 7A (294 meq), there are added 30 g (294 meq) of dimethyl ethanolamine sold under the mark "AMIETOL M 21". The mixture is heated with agitation and under a nitrogen atmosphere at 130° C. for 7 hours. The reaction rate, determined by dosage of the quaternary ammonium chlorides, is 89%.

The product obtained is provided in the form of a deep brown colored, very soft paste which is very dispersible in water. After addition of a mineral or organic acid, the solution presents no more than a very slight opalescence.

Base Index: 0.73 meq/g.
Ionized Chloride: 3 meq/g.

EXAMPLE 8A

Preparation of a polytertiobutoxy bisequenced oligomer intermediate of the formula

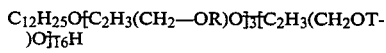

wherein R is dodecyl and T is tertiobutyl.

To 9.3 g (50 meq) of dodecanol, sold under the mark "ALFOL 12", there are added over a 35 minute period, at a temperature of 75° C., 0.12 ml of $BF_3$ etherate and 36.2 g of dodecyl glycidyl ether (150 meq).

This temperature and agitation are maintained for 1 hour.

One checks by dosage that all the epoxide has been consumed. There are then added, over a period of 1 hour and 55 minutes, at 85° C., 0.9 ml of $BF_3$ etherate and then 104 g of tertiobutyl glycidyl ether (800 meq). After 3 hours of agitation at 85° C., the reaction is practically complete.

The product is provided in the form of a pale yellow oil.

EXAMPLE 8B

Preparation of a nonionic bisequenced oligomer of the formula

wherein R is dodecyl.

To 75 g (400 meq) of the polytertiobutoxy derivative prepared in Example 8A, there is added 2% sulfoacetic acid. The mixture is heated to 80°–100° C.

At this temperature a significant evolution of isobutylene is noted. There are then added, by fractions, 30 ml of water. Total duration of heating: 5½ hours.

The reaction mass is diluted with 500 ml of water and the acidity is neutralized with 60 g of a basic ion exchange resin sold under the mark "AMBERLITE". The reaction mixture is filtered and the water is distilled under reduced pressure.

There are thus obtained 57 g of a high viscosity, deep brown colored product.

Hydroxyl Index: 7.45 meq/g.
Cloud point in butyl diglycol: 25° C.

EXAMPLE 9A

Preparation of a polyhalogenated trisequenced oligomer intermediate of the formula

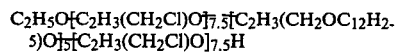

To 4.6 g of absolute ethanol (100 meq), there are added in two fractions, alternately, 0.37 ml of $BF_3$ etherate and 69.4 g of epichlorohydrin (750 meq) at a temperature of 60° C.

After 1 hour of agitation at 60° C., there are added, alternately in three fractions, 0.3 ml of $BF_3$ etherate and and 125 g (500 meq) of dodecyl glycidyl ether. Agitation of the mixture at a temperature of 70° C. is maintained for 2 hours. There are finally added, in two fractions, always at 60°–70° C., 1.8 ml of $BF_3$ etherate and 69.5 g (750 meq) of epichlorohydrin.

The product thus obtained is washed three times with 400 ml of boiling water and then dehydrated under reduced pressure. After removal of the volatile materials by molecular distillation at 225° C., a product having a molecular weight of 1,475 is obtained. Its hydroxyl index is 0.7 meq/g. The amount of organic chloride is 5.6 meq/g.

EXAMPLE 9B

Preparation of a cationic trisequenced oligomer of the formula

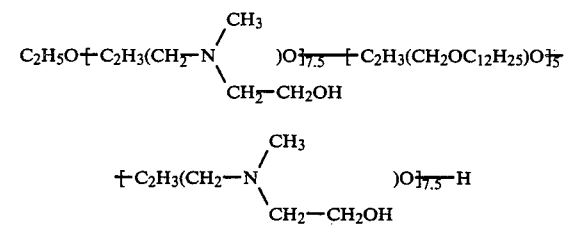

To 53.5 g of the polyhalogenated derivative prepared in Example 9A (300 meq chloride), there are added 60 g (750 meq) of methylethanolamine, sold under the mark "AMIETOL M 11".

After 6 hours of heating at 130° C., the reaction is practically complete. After dilution with 120 ml of isopropanol, the HCl formed is neutralized with 29.5 g of sodium hydroxide (10.6 meq/g).

The product is then filtered and the isopropanol is distilled under reduced pressure. The product thus obtained exhibits very slight cloudiness in water. This cloudiness disappears completely on the addition of a small amount of a mineral or organic acid.

Base Index: 4.4 meq/g.
Hydroxyl Index: 4.6 meq/g.

EXAMPLE 9C

Preparation of a nonionic trisequenced oligomer of the formula

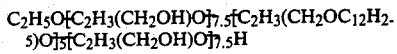

To 60 g (336 meq) of the polyhalogenated derivative prepared in Example 9A, there are added 60 g of dietheyleneglycol, and 34.5 g of potassium acetate (330 meq). The mixture is heated under a nitrogen atmosphere at 185° C. for 7 hours. The potassium chloride is filtered and the diethyleneglycol is removed by distillation under reduced pressure.

The product is then submitted to alcoholysis in 60 ml of absolute ethanol in the presence of 0.5 g of sodium methylate (5.5 meq/g), for 12 hours at ambient temperature.

After distillation of the ethanol there is obtained a deep colored product which is very dispersible in water. Its hydroxyl index is 7.4 meq/g and its cloud point in butyl diglycol is 80° C.

EXAMPLE 10A

Preparation of a polyhalogenated trisequenced oligomer of the formula

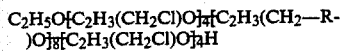

wherein R is a mixture of $C_{11}$ and $C_{13}$ alkyls.

To 4.6 g of absolute ethanol (100 meq), there are added at 60° C., 0.33 ml of $SnCl_4$ and 37 g (400 meq) of epichlorohydrin.

After 1 hour of agitation at 60° C., there are added alternately in three fractions, 1.5 ml of $SnCl_4$ and 190 g (800 meq) of a mixture of epoxy tetradecane and epoxy hexadecane, approximately in the proportions 2.72:1, sold under the mark "EPOXYDE 16".

After having verified that all the epoxide is consumed, there are added again, 0.33 ml of $SnCl_4$ and 37 g (400 meq) of epichlorohydrin.

The product thus obtained is washed three times with 300 ml of boiling water and then dehydrated under reduced pressure.

The product is in the form of a slightly colored oil whose hydroxyl index is 0.7 meq/g. The amount of organic chloride is 2.9 meq/g.

EXAMPLE 10B

Preparation of a nonionic trisequenced oligomer of the formula

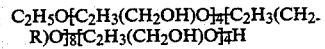

wherein R is a mixture of $C_{11}$ and $C_{13}$ alkyls.

To 60 g of the polyhalogenated derivative prepared in Example 10A (175 meq), there are added 60 g of dipropylene glycol and 18.5 g of potassium acetate.

The reaction mixture is then heated under a nitrogen atmosphere at 185° C. for 6 hours. The reaction is then practically complete. The potassium chloride is filtered and the dipropylene glycol is removed by distillation under reduced pressure.

The thus formed acetic ether is then subjected to alcoholysis in 600 ml of absolute ethanol, in the presence of 0.5 g of sodium methylate (5.4 meq/g) overnight at ambient temperature.

The ethanol is removed by distillation and the resulting product is slightly colored.

Hydroxyl Index: 4 meq/g.

EXAMPLE 11A

Preparation of a polyhalogenated trisequenced oligomer of the formula

To 4.6 g of absolute ethanol (100 meq), there are added, alternately in three fractions, at a temperature of 75° C., 0.4 ml of $BF_3$ etherate and 92.5 g (1 mole) of epichlorohydrin.

After all the epichlorohydrin has been consumed, there are added, alternately in three fractions, 0.4 ml of $BF_3$ etherate and 125 g (500 meq) of dodecyl glycidyl ether.

After 1 hour of agitation at 80° C., there are finally added again, in three fractions, 0.4 ml of $BF_3$ etherate and 92.5 g of epichlorohydrin.

The halogenated product thus prepared is washed three times with 350 ml of boiling water and then dried under reduced pressure.

The product obtained is present in the form of a brown oil, whose hydroxyl index is 1 meq/g. The amount of organic chloride is 6.25 meq/g.

EXAMPLE 11B

Preparation of a nonionic trisequenced oligomer of the formula

To 60 g of the polyhalogenated derivative prepared in Example 11A (380 meq-chloride), there are added 60 g of diethylene glycol and 39 g of potassium acetate.

The reaction mass is heated under a nitrogen atmosphere for 6 hours at 180° C.

After filtration of the potassium chloride and removal of the diethylene glycol, there are added 60 ml of absolute ethanol and 2.2 g of sodium methylate (1.2 meq/g).

After standing overnight at ambient temperature, the ethanol is removed by distillation.

The product is incompletely soluble in water and its cloud point in butyl diglycol is 97° C.

On treatment of a 5% aqueous solution of this product with an equivalent weight of ethyl acetate, a product which is perfectly soluble in water is obtained.

EXAMPLE 12A

Preparation of a polyhalogenated bisequenced oligomer of the formula

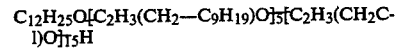

To 13.9 g (0.075 mole) of dodecanol, sold under the mark "ALFOL 12", there is added, initially, 0.33 ml of $BF_3$ etherate and then at 50°–55° C. there are added with agitation, over a period of 1½ hours, 69 g (0.375 mole) of epoxydodecane. This mixture is left to stand with agitation for 1 hour at 55° C.

There is initially added 0.6 ml of BF$_3$ etherate and then at 55° C., with agitation, there are added over a 2 hour period, 104 g (1.125 mole) of epichlorohydrin.

The mixture is then maintained at this temperature with agitation for 2 hours.

The product thus obtained is washed three times with 200 ml of boiling water and then dehydrated by heating it under reduced pressure. It is then stripped by molecular distillation at 225° C. under 10$^{-3}$ mm Hg.

EXAMPLE 12B

Preparation of a cationic bisequenced oligomer of the formula

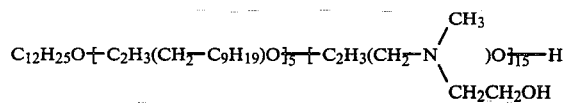

To 60 g of the polyhalogenated derivative prepared in Example 12A (361 meq-chloride), there are added 72.5 g of methyl ethanolamine (902 meq) The mixture is heated for 5 hours at 130° C. under a nitrogen atmosphere. The reaction rate is 100%.

The product obtained is washed three times with 150 ml of boiling water. After entraining the water vapor, it is dehydrated by heating it under reduced pressure.

The final product is present in the form of a brown colored thick oil, soluble in water, with a slight opalescence which disappears by the addition of a small amount of acid.

Base Index, Total: 4.40–4.55 meq/g.
Tertiary Amine Index: 4.43–4.76 meq/g.

Examples of Use

EXAMPLE A1

A nonionic shampoo composition is prepared by admixing the following components:

| | |
|---|---|
| Compound of Example 1B | 2 g |
| R—CHOH—CH$_2$O—[CH$_2$—CHOH—CH$_2$O]$_{3.5}$H wherein R is a mixture of C$_9$-C$_{12}$ alkyls | 6 g |
| Lauryl alcohol polyoxyethylenated with 12 moles of ethylene oxide per mole of alcohol | 7 g |
| Diethanolamide of the fatty acids of copra | 2 g |
| Water, sufficient for | 100 g | pH=5 Clear solution.

EXAMPLE A2

A nonionic shampoo composition is prepared by admixing the following components:

| | |
|---|---|
| Compound of Example 4B | 2 g |
| R—CHOH—CH$_2$—O—[CH$_2$CHOH—CH$_2$O]$_{3.5}$H wherein R is a mixture of C$_9$-C$_{12}$ alkyls | 6 g |
| Lauryl alcohol polyoxyethylenated with 12 moles of ethylene oxide | 7 g |
| Diethanolamide of the fatty acids of copra | 2 g |
| Water, sufficient for | 100 g | pH=5 Clear solution.

EXAMPLE A3

A nonionic shampoo composition is prepared by admixing the following components:

| | |
|---|---|
| Compound of Example 9B | 2 g |
| C$_{12}$H$_{25}$O—[C$_2$H$_3$O(CH$_2$OH)$_4$]—H | 7 g |
| Lauryl alcohol polyoxyethylenated with 12 moles of ethylene oxide | 7 g |
| Lauric diethanolamide | 3 g |
| Water, sufficient for | 100 g | pH=5 Clear solution.

EXAMPLE A4

A nonionic shampoo composition is prepared by admixing the following components:

| | |
|---|---|
| Compound of Example 7B | 2 g |
| C$_{12}$H$_{25}$O—[C$_2$H$_3$O(CH$_2$OH)]—$_4$H | 7 g |
| Lauryl alcohol polyoxyethylenated with 12 moles of ethylene oxide | 7 g |
| Lauric diethanolamide | 3 g |
| Water, sufficient for | 100 g | pH=5 Clear solution.

EXAMPLE A5

A cationic shampoo composition is prepared by admixing the following components:

| | |
|---|---|
| Compound of Example 1B | 2 g |
| C$_{12}$-C$_{18}$ alkyl dimethylammoniacetate, sold under the name "DEHYTON AB 30" | 10 g |
| Lauryl alcohol polyoxyethylenated with 12 moles of ethylene oxide | 3 g |
| Diethanolamide of the fatty acids of copra | 2 g |
| Water, sufficient for | 100 g | pH=5 Clear solution.

EXAMPLE A6

An anionic shampoo composition is prepared by admixing the following components:

| | |
|---|---|
| Compound of Example 1B | 1 g |
| C$_{12}$-C$_{14}$ alkyl sodium ether sulfate oxyethylenated with 2.2 moles of ethylene oxide | 25 g |
| Hydroxypropyl methyl cellulose | 0.2 g |
| Water, sufficient for | 100 g | pH=8.5 Clear solution.

EXAMPLE B1

A cream hair dye composition containing oxidation dyes is prepared from an admixture of the following components:

| | |
|---|---|
| Carrier | |
| Compound of Example 4B | 5 g |
| Cetyl stearyl alcohol | 20 g |
| Sodium cetyl stearyl sulfate | 5 g |
| Ammonium lauryl sulfate (20% fatty alcohol) | 10 g |
| Ammonia-22° Be' | 12 ml |
| Dyes | |
| Metadiamino anisol sulfate | 0.048 g |
| Resorcinol | 0.420 g |
| Meta-aminophenol base | 0.150 g |
| Nitro p-phenylene diamine | 0.085 g |
| Para tolyulene diamine | 0.004 g |
| Ethylene diamine tetra acetic acid | 1 g |
| Sodium bisulfite, d = 1.32 | 1.200 g |

| | |
|---|---|
| Water, sufficient for | 100 g |

30 g of this cream are mixed in a bowl with 45 g of H$_2$O$_2$ (20 vol—about 6 weight percent). A smooth cream, pleasant to apply and which adheres well to the hair is thus obtained. The pH of that cream is 9.7-9.8.

This cream is applied to the hair with the aid of a brush and it is permitted to remain in contact with the hair for 30 minutes. The hair which is then rinsed, untangles easily and is silky to the touch. The hair after setting and drying, is shiny and lively; it has a silky feel and it combs easily. On 100% white hair a blonde coloration is obtained.

EXAMPLE B2

A cream hair dye composition containing oxidation dyes is prepared from an admixture of the following components:

| Carrier | |
|---|---|
| Compound of Example 9B | 6 g |
| Cetyl stearyl alcohol | 18 g |
| Sodium cetyl stearyl sulfate | 4 g |
| Ammonium lauryl sulfate (20% fatty alcohol) | 12 g |
| Ammonia-22° Be' | 13 ml |
| Dyes | |
| Metadiamino anisol sulfate | 0.048 g |
| Resorcinol | 0.420 g |
| Meta amino phenol base | 0.150 g |
| Nitro p-phenylene diamine | 0.085 g |
| Paratoluylene diamine | 0.004 g |
| Ethylenediamine tetraacetic acid | 1 g |
| Sodium bisulfite, d = 1.32 | 1.200 g |
| Water, sufficient for | 100 g |

30 g of this cream are mixed in a bowl 45 g of H$_2$O$_2$, 20 volumes. A smooth cream, pleasant to apply and which adheres well to the hair is thus obtained. Its pH is 9.7-9.8.

This cream is applied to the hair with the aid of a brush and is permitted to remain in contact with the hair for 30 minutes. The hair, after rinsing, combs easily and is silky to the touch. The hair is then set and dried. The hair thus treated is shiny and lively; it has a silky touch and it combs easily. On 100% white hair a blonde coloration is obtained.

EXAMPLE B3

A cream hair dye composition containing oxidation dyes is prepared from an admixture of the following components:

| Carrier | |
|---|---|
| Compound of Example 7B | 5 g |
| Cetyl stearyl alcohol | 22 g |
| Sodium cetyl stearyl sulfate | 6 g |
| Ammonium lauryl sulfate (20% fatty alcohol) | 11 g |
| Ammonia-22° Be' | 14 ml |
| Dyes | |
| Metadiamino anisol sulfate | 0.048 g |
| Resorcinol | 0.420 g |
| Meta-aminophenol base | 0.150 g |
| Nitro p-phenylene diamine | 0.085 g |
| Ethylene diamine tetraacetic acid | 1 g |
| Sodium bisulfite, d = 1.32 | 1.200 g |
| Water, sufficient for | 100 g |

30 g of this cream are mixed in a bowl with 45 g of H$_2$O$_2$ (20 volumes). A smooth, consistent, cream which is pleasant to use and which adheres well to the hair is thus obtained. Its pH is 9.7-9.8.

This cream is applied to the hair with the aid of a brush and is permitted to remain in contact with the hair for 30 minutes. The hair, after rinsing, combs easily and has a silky touch. The hair after setting and drying is shiny and lively; it has a silky touch; and it combs easily. On 100% white hair a blonde coloration is obtained.

What is claimed is:

1. A polysulfoxide non-ionic bisequenced oligomer of the formula:

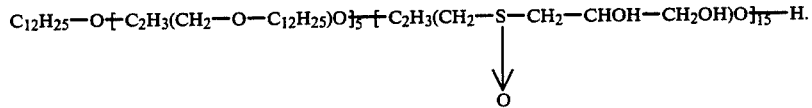

2. A polysulfoxide non-ionic bisequenced oligomer of the formula:

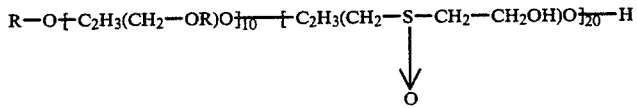

wherein R is 2-ethylhexyl.

3. A polylsulfoxide non-ionic bisequenced oligomer of the formula:

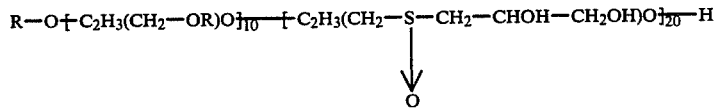

wherein R is 2-ethylhexyl.

4. A polythioether non-ionic bisequenced oligomer of the formula:

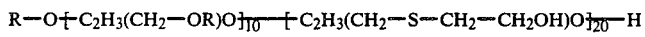

wherein R is 2-ethylhexyl.

5. A bisequenced oligomer surfactant of the formula

wherein
$[C_2H_3(CH_2A)O]$ represents the two isomers:

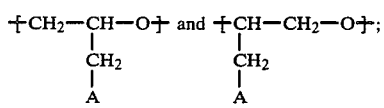

$[C_2H_3(CH_2B)O]$ represents the two isomers:

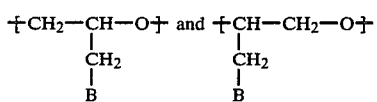

P represents linear or branched alkyl having 1–20 carbon atoms;

A represents $R-CH_2-$ or $R'-O-$, wherein R represents linear alkyl having from 4–16 carbon atoms and R' represents linear or branched alkyl having from 4–20 carbon atoms;

B represents

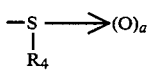

wherein a represents 0 or 1 and $R_4$ represents alkyl having 1–3 carbon atoms, hydroxyalkyl having 1–3 carbon atoms or dihydroxyalkyl having 2–3 carbon atoms;

m represents a whole or decimal number from 2 to 10; and n represents a whole or decimal number from 2 to 25.

6. A bisequenced oligomer surfactant of the formula

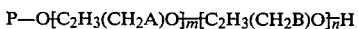

wherein
$\{C_2H_3(CH_2A)O\}$ represents the two isomers:

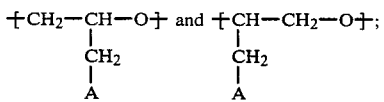

$[C_2H_3(CH_2B)O]$ represents the two isomers:

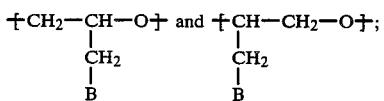

P represents linear or branched alkyl having 1–20 carbon atoms;

A represents $R-CH_2-$ or $R'-O-$ wherein R represents linear alkyl having from 4–16 carbon atoms and R' represents linear or branched alkyl having from 4–20 carbon atoms;

B represents $-S-R_4$ wherein $R_4$ represents alkyl having 1–3 carbon atoms, hydroxyalkyl having 1–3 carbon atoms or dihydroxyalkyl having 2–3 carbon atoms;

m represents a whole or decimal number from 2 to 10; and n represents a whole or decimal number from 2 to 25.

7. A bisequenced oligomer surfactant of the formula

wherein
$\{C_2H_3(CH_2A)O\}$ represents the two isomers:

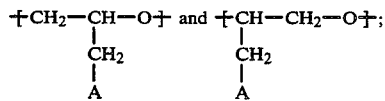

$[C_2H_3(CH_2B)O]$ represents the two isomers

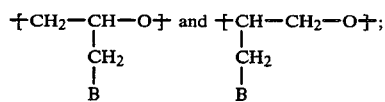

P represents linear or branched alkyl having 1–20 carbon atoms;

A represents $R-CH_2-$ or $R'-O-$ wherein R represents linear alkyl having from 4–16 carbon atoms and R' represents linear or branched alkyl having from 4–20 carbon atoms;

B represents

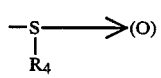

wherein
$R_4$ represents alkyl having 1–3 carbon atoms, hydroxyalkyl having 1–3 carbon atoms or dihydroxyalkyl having 2–3 carbon atoms;

m represents a whole or decimal number from 2 to 10; and n represents a whole or decimal number from 2 to 25.

8. A bisequenced oligomer surfactant of the formula

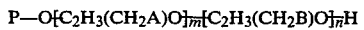

wherein
$\{C_2H_3(CH_2A)\}$ represents the two isomers:

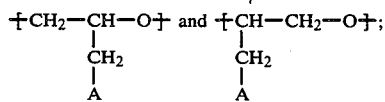

$\{C_2H_3(CH_2B)O\}$ represents the two isomers:

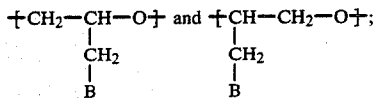

P represents linear or branched alkyl having 1–20 carbon atoms;
A represents R—CH$_2$— or R′—O—, wherein R represents linear alkyl having from 4–16 carbon atoms and R′ represents linear or branched alkyl having from 4–20 carbon atoms;
B represents

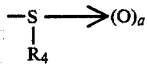

wherein a represents 0 or 1 and R$_4$ represents hydroxyalkyl having 1–3 carbon atoms or dihydroxyalkyl having 2–3 carbon atoms;
m represents a whole or decimal number from 2 to 10; and
n represents a whole or decimal number from 2 to 25.

9. A bisequenced oligomer surfactant of the formula

wherein
[C$_2$H$_3$(CH$_2$A)O] represents the two isomers:

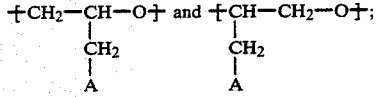

—[C$_2$H$_3$(CH$_2$B)O]—represents the two isomers:

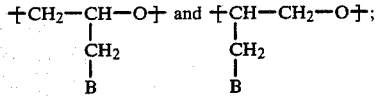

P represents linear or branched alkyl having 1–20 carbon atoms;
A represents R—CH$_2$— or R′—O— wherein R represents linear alkyl having from 4–6 carbon atoms and R′ represents linear or branched alkyl having from 4–20 carbon atoms;
B represents —S—R$_4$ wherein R$_4$ represents hydroxyalkyl having 1–3 carbon atoms or dihydroxyalkyl having 2–3 carbon atoms;
m represents a whole or decimal number from 2 to 10; and
n represents a whole or decimal number from 2 to 25.

10. A bisequenced oligomer surfactant of the formula

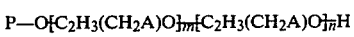

wherein
—[C$_2$H$_3$(CH$_2$A)O]—represents the two isomers:

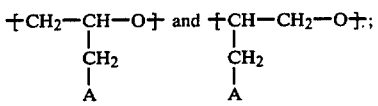

—[C$_2$H$_3$(CH$_2$B)O]— represents the two isomers

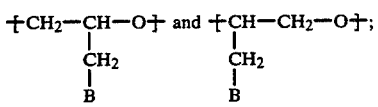

P represents linear or branched alkyl having 1–20 carbon atoms;
A represents R—CH$_2$— or R′—O— wherein R represents linear alkyl having from 4–16 carbon atoms and R′ represents linear or branched alkyl having from 4–20 carbon atoms;
B represents

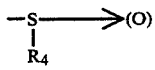

wherein R$_4$ represents hydroxyalkyl having 1–3 carbon atoms or dihydroxyalkyl having 2–3 carbon atoms;
m represents a whole or decimal number from 2 to 10; and
n represents a whole or decimal number from 2 to 25.

* * * * *